United States Patent
Searfoss et al.

(10) Patent No.: US 10,918,394 B2
(45) Date of Patent: Feb. 16, 2021

(54) RADIAL ARTERY COMPRESSION BAND HAVING FINE ADJUSTMENT MECHANISM

(71) Applicant: Oscor Inc., Palm Harbor, FL (US)

(72) Inventors: Timothy Searfoss, New Port Richey, FL (US); Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 311 days.

(21) Appl. No.: 16/156,696

(22) Filed: Oct. 10, 2018

(65) Prior Publication Data

US 2020/0113579 A1   Apr. 16, 2020

(51) Int. Cl.
*A61B 17/132* (2006.01)
*A61B 17/12* (2006.01)

(52) U.S. Cl.
CPC *A61B 17/1327* (2013.01); *A61B 2017/12004* (2013.01)

(58) Field of Classification Search
CPC ........ A61F 5/028; A61F 5/30; A61B 17/1325; A61B 17/1327; A61B 2017/00889; A61B 2017/12004
See application file for complete search history.

(56) References Cited

U.S. PATENT DOCUMENTS

| | | |
|---|---|---|
| 2,367,690 A | 1/1945 | Purdy |
| 4,182,338 A | 1/1980 | Stanulis |
| 5,010,902 A * | 4/1991 | Rambo .............. A61B 17/1325 128/112.1 |
| 5,269,803 A | 12/1993 | Geary et al. |
| 5,728,120 A * | 3/1998 | Shani ................. A61B 17/1325 606/120 |
| 7,498,477 B2 | 3/2009 | Wada et al. |
| 8,353,927 B2 | 1/2013 | Lampropoulos et al. |
| 8,657,850 B2 | 2/2014 | McNeese |
| D705,428 S | 5/2014 | Cheney et al. |
| 8,845,680 B2 | 9/2014 | Lampropoulos et al. |
| 9,107,671 B2 | 8/2015 | Guillot |
| 9,463,026 B2 | 10/2016 | Corrigan, Jr. |
| 9,743,934 B2 | 8/2017 | Lampropoulos et al. |
| 9,895,155 B2 | 2/2018 | Wada et al. |
| 2012/0053617 A1* | 3/2012 | Benz ................. A61B 17/1327 606/203 |

* cited by examiner

*Primary Examiner* — Mohamed G Gabr
(74) *Attorney, Agent, or Firm* — Locke Lord LLP; Scott D. Wofsy

(57) ABSTRACT

A radial artery compression band is disclosed for circumferential placement around the wrist of a patient to apply hemostasis pressure to a wound, which includes a first arcuate band portion including a radially outwardly extending support frame, a second elongated band portion including a plurality of longitudinally spaced apart radially outwardly extending ramped engagement teeth, a third elongated band portion extending between the first and second band portions and including a radially inwardly facing compression structure for applying hemostasis pressure to the wound, and a band adjustment mechanism mounted within the support frame of the first arcuate band portion and including an axially rotatable shaft having a worm gear section with a continuous helical thread for selectively intermeshing with the ramped engagement teeth on the second elongated band portion to adjust band tension through axial rotation of the shaft.

16 Claims, 4 Drawing Sheets

RADIAL ARTERY COMPRESSION BAND HAVING FINE ADJUSTMENT MECHANISM

BACKGROUND OF THE INVENTION

1. Field of the Invention

The subject invention is directed to a compressive hemostatic device, and more particularly, to a radial artery compression band for precisely applying hemostasis pressure to a vascular intervention site following a radial artery procedure.

2. Description of Related Art

Vascular intervention procedures have long been performed by accessing the femoral artery. However, access of the radial artery has become accepted as an alternative to femoral artery intervention for certain intervention procedures. For example, radial artery access for cardiac catheterization has become an accepted intervention procedure. Indeed, it has been found that intervention of the radial artery reduces costs and potential complications when compared to femoral artery invention.

Following the intervention, hemostasis of the access site is achieved by applying a hemostasis compression band to the site or by applying manual pressure to the site. However, certain deficiencies exist with respect to conventional devices used to provide hemostasis of a radial access site. For instance, conventional hemostasis devices (including compression bands), while being able to provide the necessary pressure to achieve hemostasis, are known to collapse the radial artery when applying pressure. It is also known that the radial artery can be occluded if the artery is either partly or completely collapsed. Occlusion of the radial artery can restrict adequate blood supply to the hand, causing complications such as pain and numbness in the hand.

It has been found that achieving hemostasis with an adjustable compression band is a more effective way to compress the radial artery just enough so that bleeding is stopped without flow obstruction in the radial artery. The present invention provides a novel hemostasis band with a mechanism that can be precisely adjusted to control the pressure that is applied to the access wound, while monitoring the pulse rate of the patient with an oximeter to confirm the proper blood flow past the access wound.

SUMMARY OF THE DISCLOSURE

The subject invention is directed to a new and useful radial artery compression band for circumferential placement around the wrist of a patient to apply hemostasis pressure to a vascular intervention site. The compression band includes a first arcuate band portion having a radially outwardly extending support frame, a second elongated band portion having a plurality of longitudinally spaced apart radially outwardly extending ramped engagement teeth, and a third elongated band portion extending between the first and second band portions and having a radially inwardly facing compression structure for applying hemostasis pressure to a vascular intervention site on a patient's wrist.

The compression band further includes a band adjustment mechanism mounted within the support frame of the first arcuate band portion and having an axially rotatable shaft including a worm gear section with a continuous helical thread for selectively intermeshing with the ramped engagement teeth on the second elongated band portion to adjust band tension through axial rotation of the shaft. Preferably, the ramped engagement teeth are angularly oriented relative to a longitudinal axis of the second band portion to intermesh mesh with the continuous helical thread of the worm gear section of the shaft.

The band adjustment mechanism is mounted for selective movement between a locked position in which the continuous helical thread of the worm gear section of the rotatable shaft is intermeshed with the engagement teeth on the second elongated band portion and an unlocked position in which the continuous helical thread of the worm gear section of the rotatable shaft is disengaged from the engagement teeth on the second elongated band portion.

Preferably, the band adjustment mechanism includes an over-centered latch member that is pivotably mounted to the support frame about a transverse pivot axis, and the support frame includes a pair of laterally spaced apart upstanding walls that pivotably support the over-centered latch member of the band adjustment mechanism therebetween. The axially rotatable shaft is rotatably connected to the over-centered latch member by a threaded fastener, and it includes a knurled handle section to facilitate manual rotation of the worm gear section of the shaft relative to the engagement teeth of the second band portion.

Preferably, the compression structure on the third band portion is a hemispherical dome, and the dome is constructed from a transparent material to enable visualization of the intervention site and accurate positioning of the dome. Furthermore, the third band portion has a radially outer surface that has a viewing port formed therein which is in communication with the hemispherical dome.

The subject invention is directed to a new and useful compression band for circumferential placement around the wrist of a patient to precisely apply hemostasis pressure to a vascular intervention site following a radial artery procedure.

BRIEF DESCRIPTION OF THE DRAWINGS

So that those skilled in the art will readily understand how to make and use the radial artery compression band of the subject invention without undue experimentation, preferred embodiments thereof will be described in detail herein below with reference to the figures wherein.

DETAILED DESCRIPTION OF THE PREFERRED EMBODIMENTS

Figure 1:
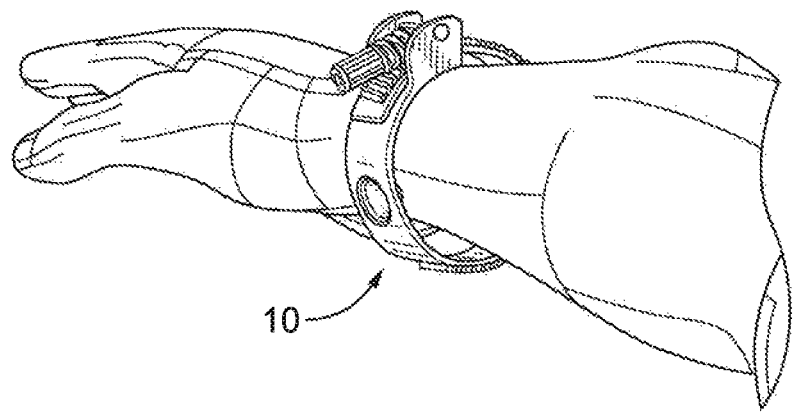
FIG. 1 is an illustration of the radial artery compression band of the subject invention placed around the wrist of a patient to apply hemostasis pressure to a vascular intervention site.
Figure 2:
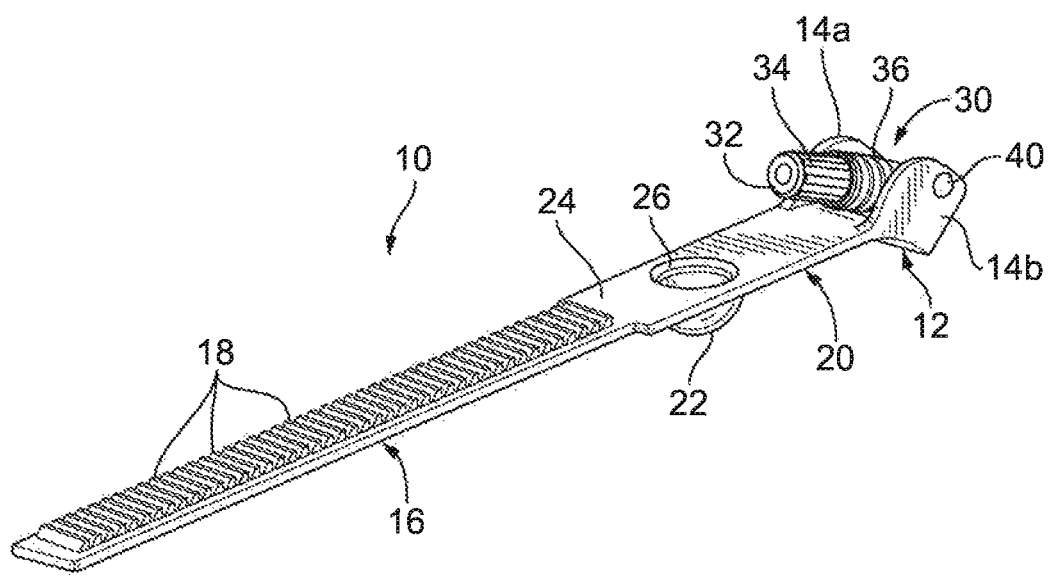
FIG. 2 is a perspective view of the radial artery compression band shown in FIG. 1 in an outstretched linear condition.

Referring now to the drawings, wherein like reference numerals identify similar structural elements of the subject invention, there is illustrated in FIG. 1 a new and useful compression band 10 for circumferential placement around the wrist of a patient to apply hemostasis pressure to a surface wound, and thereby constrict blood loss following a radial artery intervention procedure.

More particularly, the compression band 10 of the subject invention is adapted and configured to provide a means for precisely adjusting pressure applied to a radial artery wound on a patient's wrist, while monitoring the patient's pulse rate with an oximeter on their finger to confirm the proper blood flow past the radial artery wound to the hand. In addition, the compression band 10 is designed to precisely adjust the pressure applied to the wound so as to prevent clotting in the artery and promote the natural healing of the wound.

Referring now to FIGS. 2 through 5, the compression band 10 of the subject invention is defined by three contiguous sections that are integrally molded from a light weight, flexible polymeric material. The first section of compression band 10 is an arcuate band portion 12 that has a support frame formed by two laterally spaced apart radially outwardly extending walls 14a and 14b. The second section of compression band 10 is an elongated band portion 16 that has a plurality of longitudinally spaced apart radially outwardly extending ramped engagement teeth 18 formed thereon. The third section of compression band 10 is an elongated band portion 20 that extends between the first and second band portions 12 and 16 and it includes a radially inwardly facing hemispherical compression dome 22 configured to apply direct hemostasis pressure to a vascular intervention site on a patient's wrist.

Preferably, the hemispherical compression dome 22 is constructed from a transparent material to enable visualization of the vascular intervention site and accurate positioning of the dome 22 at the precise location of the wound. More particularly, the medial portion 20 of compression band 10 has a radially outer surface 24 that includes a circular viewing port 26 which communicates with the transparent compression dome 22. The circular viewing port 26 provides a way to accurately position the compression dome 22 relative to the wound.

The compression band 10 of the subject invention further includes a manually operable fine adjustment mechanism 30 that is mounted between the support frame walls 14a and 14b of the first band portion 12. The adjustment mechanism 30 provides a way to precisely control and apply pressure to the surface of the intervention wound to promote hemostasis, while not restricting the flow of blood through the radial artery so as to inadvertently cause an occlusion.

The adjustment mechanism 30 is adapted and configured to enable the compression band 10 to be utilized on a wide variety of wrist sizes. Preferably, the compression band 10 is dimensioned so that it can be used by patients having wrist sizes of about 3.8 inches to about 8.5 inches in circumference.

Figure 3:
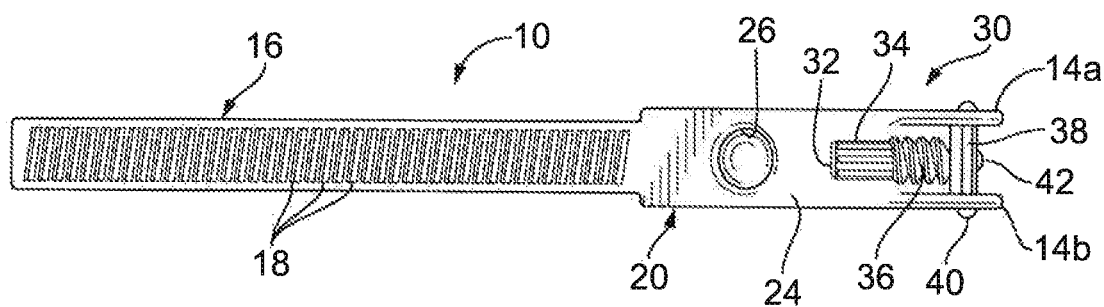
FIG. 3 is a top plan view of the radial artery compression band in the outstretched linear condition shown in FIG. 2, illustrating the radially outer surface features of the band.
Figure 4:
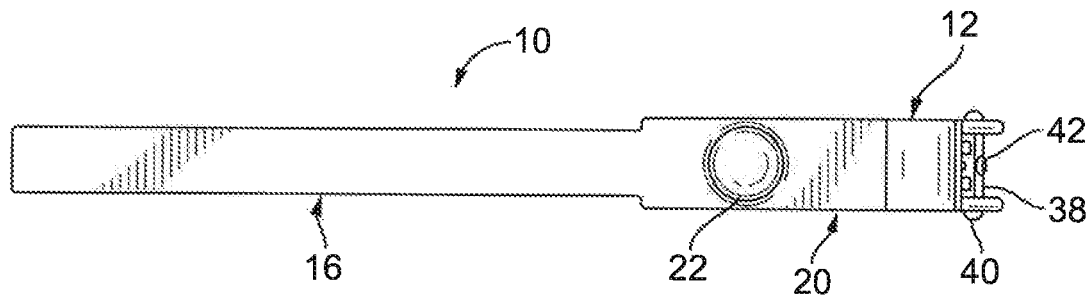
FIG. 4 is a bottom plan view of the radial artery compression band in the outstretched linear condition shown in FIG. 2, illustrating the radially inner surface features of the band.
Figure 5:
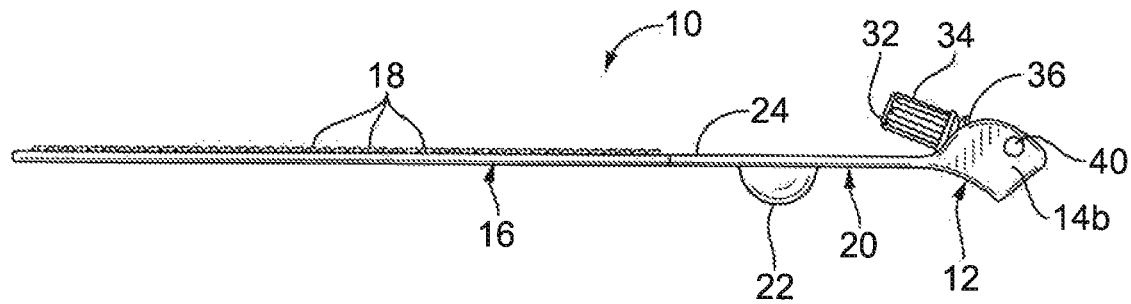
FIG. 5 is a side elevational view of the radial artery compression band in the outstretched linear condition shown in FIG. 2.

The fine adjustment mechanism 30 includes a manually rotatable shaft 32 that has a generally cylindrical knurled handle section 34 and an elongated worm gear section 36. The worm gear section 36 includes a continuous helical thread that is configured to intermesh with the ramped engagement teeth 18 formed on the second band portion 16 to adjust band tension and thereby adjust a degree of hemostasis pressure applied to the intervention site by the compression dome 22. As best seen in FIG. 3, the engagement teeth 18 on the second band portion 16 are angularly oriented relative to a longitudinal axis of the outstretched second band portion 16 so as to readily mesh with the continuous helical thread of the worm gear section 36 of shaft 32.

Figure 6:
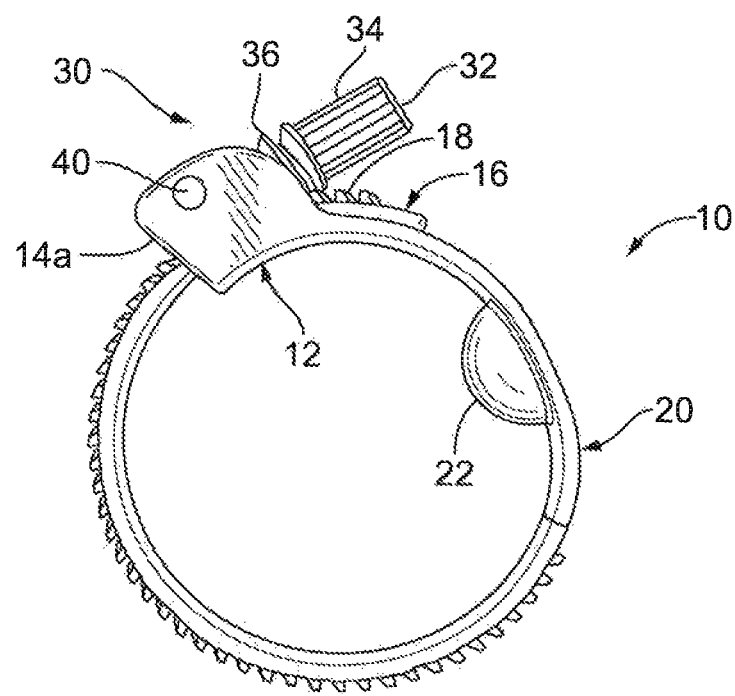
FIG. 6 is a side elevational view of the radial artery compression band in a closed circular condition as shown in FIG. 1, with the adjustment mechanism in a locked or engaged position.
Figure 7:
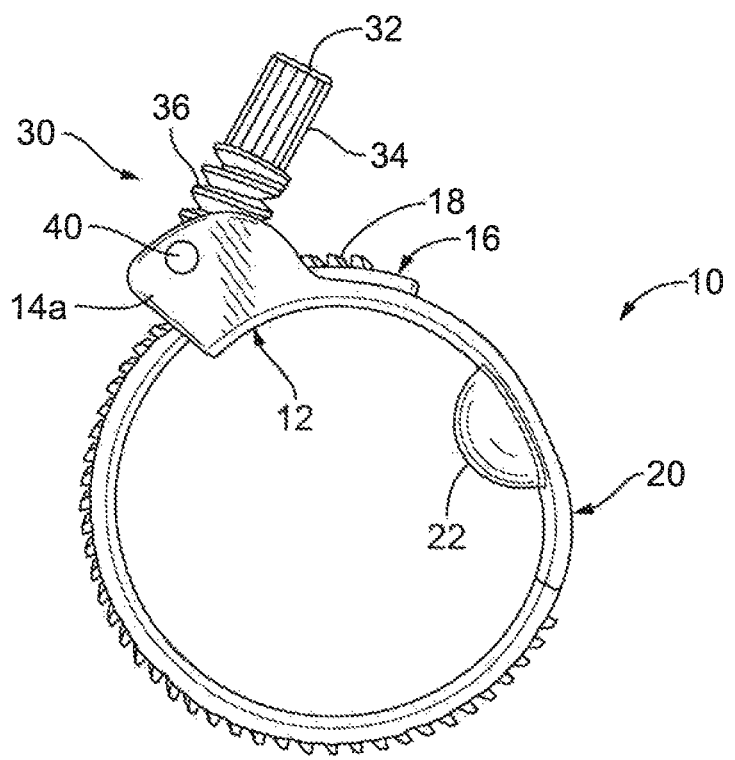
FIG. 7 is a side elevational view of the radial artery compression band in a closed circular condition as shown in FIG. 1, with the adjustment mechanism in an unlocked or disengaged position.

Preferably, the adjustment mechanism 30 is mounted for movement between a locked position, which is shown in FIG. 6, and an unlocked position, which is shown in FIG. 7. In the locked position shown in FIG. 6, the continuous helical thread of the worm gear section 36 of shaft 32 is intermeshed with the engagement teeth 18 on the second band portion 16, and fine tension adjustments can be made by axially rotating shaft 32. In the unlocked position shown in FIG. 7, the continuous helical thread of the worm gear section 36 of shaft 32 is disengaged from the engagement teeth 18 of the second band portion 16 and any tension in the band is released.

Figure 8:
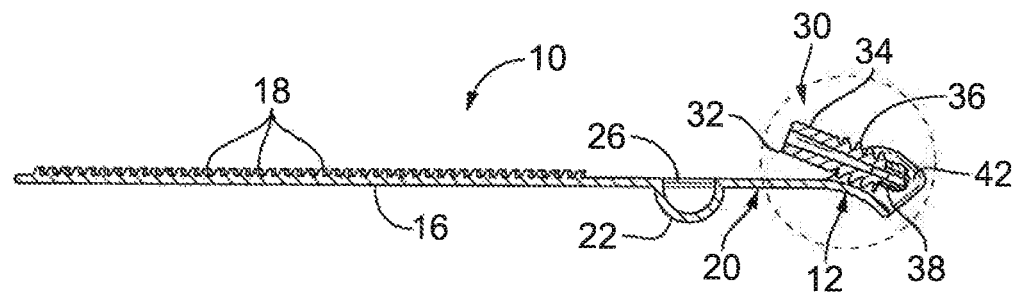
FIG. 8 is a cross-sectional view taken along line 8-8 of FIG. 4.
Figure 9:
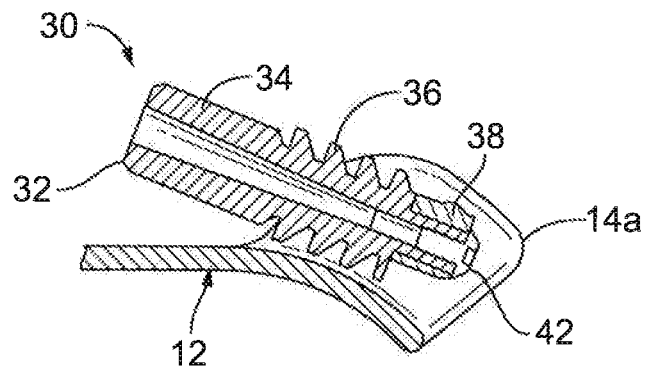
FIG. 9 is an enlarged localized view from FIG. 8.
Figure 10:
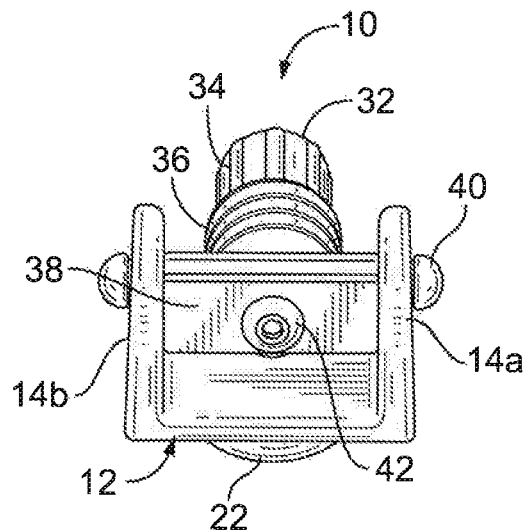
FIG. 10 is a rear end view of the radial artery compression band.
Figure 11:
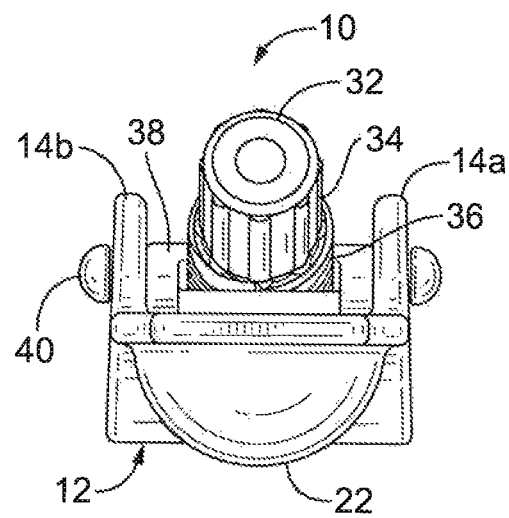
FIG. 11 is a front end view of the radial artery compression band.

Referring to FIGS. 10 and 11, the adjustment mechanism 30 further includes an over-centered latch member 38 that is pivotably mounted between the support frame walls 14a and 14b of band portion 12 for movement about a transverse pivot axis 40. The shaft 32 is rotatably connected to the over-centered latch member 38 by a threaded fastener 42, as shown in in the cross-sectional views of FIGS. 8 and 9.

The over-centered latch member 38 provides a means to ensure that the adjustment mechanism 30 remains in the locked position of FIG. 6, so that the compression dome 22 is retained in the desired location on the patient wrist relative to the wound. The latch member 38 also provides a means for readily releasing the adjustment mechanism 30 in the event the compression band 10 needs to be quickly removed from a patient's wrist to prevent radial artery occlusion or when the wound has healed sufficiently and the compression band is no longer needed.

While the subject disclosure has been shown and described with reference to preferred embodiments, those skilled in the art will readily appreciate that changes or modifications may be made thereto without departing from the spirit or scope of the subject disclosure.

What is claimed is:

1. A radial artery compression band for circumferential placement around the wrist of a patient to apply hemostasis pressure to a vascular intervention site, comprising:
   a) a first arcuate band portion including a radially outwardly extending support frame;
   b) a second elongated band portion including a plurality of longitudinally spaced apart radially outwardly extending ramped engagement teeth;
   c) a third elongated band portion extending between the first and second band portions and including a radially inwardly facing compression structure for applying hemostasis pressure to a vascular intervention site on a patient's wrist; and d) a band adjustment mechanism mounted within the support frame of the first arcuate band portion and including an axially rotatable shaft having a worm gear section with a continuous helical thread for selectively intermeshing with the ramped engagement teeth on the second elongated band portion to adjust band tension through axial rotation of the shaft, wherein the band adjustment mechanism is mounted for selective movement between a locked position in which the continuous helical thread of the worm gear section of the rotatable shaft is intermeshed with the engagement teeth on the second elongated band portion and an unlocked position in which the continuous helical thread of the worm gear section of the rotatable shaft is disengaged from the engagement teeth on the second elongated band portion, and wherein the band adjustment mechanism includes an over-centered latch member that is pivotably mounted to the support frame about a transverse pivot axis.

2. A radial artery compression band as recited in claim 1, wherein the support frame includes a pair of laterally spaced apart upstanding walls that pivotably support the over-centered latch member of the band adjustment mechanism therebetween.

3. A radial artery compression band as recited in claim 1, wherein the axially rotatable shaft is rotatably connected to the over-centered latch member by a threaded fastener.

4. A radial artery compression band as recited in claim 1, wherein the axially rotatable shaft includes a knurled handle section to facilitate manual rotation of the worm gear section of the shaft relative to the engagement teeth of the second band portion.

5. A radial artery compression band as recited in claim 1, wherein the engagement teeth are angularly oriented relative to a longitudinal axis of the second band portion to mesh with the continuous helical thread of the worm gear section of the shaft.

6. A radial artery compression band as recited in claim 1, wherein the compression structure on the third band portion is a hemispherical dome.

7. A radial artery compression band as recited in claim 6, wherein the hemispherical dome is constructed from a transparent material to enable visualization of the intervention site and accurate positioning of the dome.

8. A radial artery compression band as recited in claim 7, wherein the third band portion has a radially outer surface that has a viewing port formed therein which is in communication with the hemispherical dome.

9. A radial artery compression band for circumferential placement around the wrist of a patient to apply hemostasis pressure to a vascular intervention site, comprising:
 a) a first arcuate band portion including a radially outwardly extending support frame having a pair of laterally spaced apart upstanding walls;
 b) a second elongated band portion including a plurality of longitudinally spaced apart radially outwardly extending ramped engagement teeth that are angularly oriented relative to a longitudinal axis of the second band portion;
 c) a third elongated band portion extending between the first and second band portions and including a radially inwardly facing hemispherical dome for applying hemostasis pressure to a vascular intervention site on a patient's wrist; and
 d) a band adjustment mechanism mounted between the upstanding walls of the support frame of the first arcuate band portion and including an axially rotatable shaft having a worm gear section with a continuous helical thread for selectively intermeshing with the angularly oriented ramped engagement teeth on the second elongated band portion to adjust band tension through axial rotation of the shaft, wherein the band adjustment mechanism is mounted for selective movement between a locked position in which the continuous helical thread of the worm gear section of the rotatable shaft is intermeshed with the engagement teeth on the second elongated band portion and an unlocked position in which the continuous helical thread of the worm gear section of the rotatable shaft is disengaged from the engagement teeth on the second elongated band portion, and wherein the band adjustment mechanism includes an over-centered latch member that is pivotably mounted to the support frame about a transverse pivot axis.

10. A radial artery compression band as recited in claim 9, wherein the axially rotatable shaft is rotatably connected to the over-centered latch member by a threaded fastener.

11. A radial artery compression band as recited in claim 9, wherein the axially rotatable shaft includes a knurled handle section to facilitate manual rotation of the worm gear section of the shaft relative to the engagement teeth of the second band portion.

12. A radial artery compression band as recited in claim 9, wherein the hemispherical dome is constructed from a transparent material to enable visualization of the intervention site and accurate positioning of the dome.

13. A radial artery compression band as recited in claim 12, wherein the third band portion has a radially outer surface that has a viewing port formed therein which is in communication with the hemispherical dome.

14. A radial artery compression band for circumferential placement around the wrist of a patient to apply hemostasis pressure to a vascular intervention site, comprising:
 a) a first arcuate band portion including a radially outwardly extending support frame having a pair of laterally spaced apart upstanding walls;
 b) a second elongated band portion including a plurality of longitudinally spaced apart radially outwardly extending ramped engagement teeth that are angularly oriented relative to a longitudinal axis of the second band portion;
 c) a third elongated band portion extending between the first and second band portions and including a radially inwardly facing hemispherical dome for applying hemostasis pressure to a vascular intervention site on a patient's wrist; and
 d) a band adjustment mechanism including an over-centered latch member pivotably mounted between the upstanding walls of the support frame of the first arcuate band portion and an axially rotatable shaft rotatably connected to the over-centered latch member by a threaded fastener, wherein the axially rotatable shaft has a knurled handle section and a worm gear section with a continuous helical thread for selectively intermeshing with the angularly oriented ramped engagement teeth on the second elongated band portion to adjust band tension through axial rotation of the shaft.

15. A radial artery compression band as recited in claim 14, wherein the over-centered latch of the band adjustment mechanism is mounted for selective movement between a locked position in which the continuous helical thread of the worm gear section of the rotatable shaft is intermeshed with the engagement teeth on the second elongated band portion and an unlocked position in which the continuous helical thread of the worm gear section of the rotatable shaft is disengaged from the engagement teeth on the second elongated band portion.

16. A radial artery compression band as recited in claim 14, wherein the hemispherical dome is constructed from a transparent material to enable visualization of the intervention site and accurate positioning of the dome, and the third band portion has a viewing port formed therein which is in communication with the hemispherical dome.

* * * * *